United States Patent [19]
Iwasaki et al.

[11] Patent Number: 5,703,234
[45] Date of Patent: Dec. 30, 1997

[54] HETEROCYCLIC ALKANAMIDE

[75] Inventors: Tameo Iwasaki, Nishinomiya; Kazuhiko Kondo, Osaka; Hiroshi Ohmizu, Kyoto, all of Japan

[73] Assignee: Tanabe Seiyaku Co., Ltd., Osaka, Japan

[21] Appl. No.: 462,676

[22] Filed: Jun. 5, 1995

Related U.S. Application Data

[62] Division of Ser. No. 262,892, Jun. 21, 1994, Pat. No. 5,550,229.

[30] Foreign Application Priority Data

Jun. 23, 1993 [JP] Japan ................. 5-151899

[51] Int. Cl.$^6$ ................. C07D 265/18; A61K 31/535
[52] U.S. Cl. ................. 544/50; 544/92; 544/287; 546/141; 514/230.5; 514/227.2; 514/311
[58] Field of Search ................. 544/50, 92, 287; 546/141

[56] References Cited

U.S. PATENT DOCUMENTS

| | | | |
|---|---|---|---|
| 4,194,047 | 3/1980 | Christensen et al. | 514/252 |
| 4,268,510 | 5/1981 | Boyle et al. | 424/248.53 |
| 5,442,055 | 8/1995 | Iwasaki et al. | 540/200 |

FOREIGN PATENT DOCUMENTS

| | | |
|---|---|---|
| 0010348 | 8/1979 | European Pat. Off. . |
| 0160391 | 11/1985 | European Pat. Off. . |
| 0213610 | 3/1987 | European Pat. Off. . |
| 0232786 | 8/1987 | European Pat. Off. . |
| 0239853 | 10/1987 | European Pat. Off. . |
| 0337637 | 10/1989 | European Pat. Off. . |
| 0474243 | 3/1992 | European Pat. Off. . |
| 0597423 | 5/1994 | European Pat. Off. . |
| 3632916 | 3/1988 | Germany . |
| 61-18779 | 1/1986 | Japan . |
| 615081 | 1/1986 | Japan . |
| 61-275267 | 12/1986 | Japan . |
| 62-169781 | 7/1987 | Japan . |
| 62-252786 | 11/1987 | Japan . |
| 63-170377 | 7/1988 | Japan . |
| 63-284176 | 11/1988 | Japan . |
| 2788 | 1/1990 | Japan . |
| 2292269 | 12/1990 | Japan . |
| 665195 | 3/1994 | Japan . |
| 9313064 | 7/1993 | WIPO . |

OTHER PUBLICATIONS

Kim et al (1987). "Stereoselective Synthesis of 1-β-Methylcarbapenem", *Tetrahedron Letters*, 28(5):507–510.

Shih et al., *Synthetic Carbapenem Antibiotics I. 1-β-Methylcarbapenem*, Heterocycles, vol. 21, No. 1, pp. 29–41, 1984.

Fuentes et al., *Lewis Acid Mediated Condensation of Chiral Imide Anolates. A General Approach to the Synthesis of Chiral Carbapenem Precursors*, Journal of the American Chemical Society, vol. 108, pp. 4675–4676, 1986.

Nagao et al., *Highly Diastereoselective Alkylation onto 4-Acetoxy-2-azetidinones Employing Tin (II) Enolates of C4-Chiral 3-Acyl-1,3-thiazolidine-2-thiones*, Journal of the American Chemical Society, vol. 108, pp. 4673–4675, 1986.

Moss et al., *A Cysteine-Functionalized Micellar Catalyst*, Tetrahedron Letters, vol. 28, No. 6, pp. 507–510, 1978.

Martel et al., *2-Picolyl thioesters; a useful synthon for the preparation of 1-β-alkyl carbepenem intermediates*, Can. J. Chem., vol. 66, pp. 1537–1539, 1988.

Endo, *Synthesis of chiral intermediates of 1-β-methylcarbapenems: (3S,4R)-3-[1(R)-tert-butyldimethylsily-loxyethyl]-4-chloroazetidin-2-one and (3S,4S)-3-[1(R)-tert-butyl-dimethylsilyloxyethyl]4-one*, Can. J. Chem., vol. 65, pp. 2140–2145, 1987.

Horrom et al., *The Condensation of Salicylamide with Aldehydes and Ketones*, Journal of the American Chemical Society, vol. 72, pp. 721–724, 1950.

Deziel et al., *Synthesis of 1-β-Methylcarbapenem Key Intermediates Involving the Labile Acyl Auxiliary 4, 4-Dimethyl-1,3-Oxazolidine-2-Thione*, vol. 30, No. 11, pp. 1345–1348, 1989.

Nagao et al; *Diastereoselective Alkylative Discrimination of Racemic 3-Substituted 4-Acetoxyazetidin-2-ones and Its Application to the Synthesis of a Chiral Key Intermediate for Carbapenem Syntheses*; Journal of Organic Chemistry; vol. 57; 1992.

(List continued on next page.)

Primary Examiner—Matthew V. Grumbling
Attorney, Agent, or Firm—Browdy and Neimark

[57] ABSTRACT

Novel process for preparing azetidinone compound of the formula [III]:

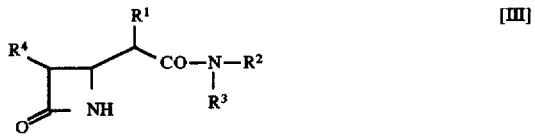

wherein $R^1$ is H or lower alkyl, $R^2$ and $R^3$ combine together with the adjacent nitrogen to form heterocyclic group, and $R^4$ is protected or unprotected hydroxy-substituted lower alkyl, which comprises reacting an alkanamide compound of the formula [I]:

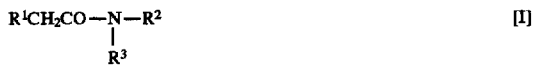

wherein $R^1$, $R^2$ and $R^3$ are the same as defined above, with a compound of the formula [II]:

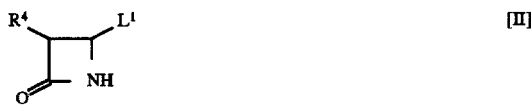

wherein $L^1$ is a leaving group and $R^4$ is the same as defined above, in the presence of a base, said compound [III] being useful as synthetic intermediate for 1-methylcarbapenem derivative having excellent antibacterial activity.

3 Claims, No Drawings

OTHER PUBLICATIONS

Ito et al; *A Novel Synthesis of the 1B–Methylcarbapenem Key Intermediate Employing the [2+2]–Clycloaddition Reaction of Chlorosulfonyl Isocyanate With a 4H–1,3–Dioxin Derivative,* Tetrahedron Letters; vol. 30, No. 41, pp. 5631–5634; 1989.

Deziel et al; *Simple and Highly Diastereoselective Synthesis of a 1B–Methycarbapenem Key Intermediate Involving Divalent Tin Enolates,* Tetrahedron Letters; vol. 27, No. 47, pp. 5687–5690; 1986.

Atsuro et al; *Patent Abstracts of Japan,* Sumitomo Pharmaceutical Co. Ltd.; vol. 11, No. 398, (C–466); 25 Dec. 1987.

Yamato et al; Reaction of 1,2,3, 4–Tetrahydroquinazolin–4–ones with Acid Anhydride. III, Chemical and Pharmaceutical Bulletin; vol. 29, No. 10, pp. 3124–3129; Oct. 1981.

Kawase; *Unusal Formation of Tetrahydro–1–isoquinolones from Tetrahydroisoquinoline–1–carboxylic Acids with Carbodiimides and Mechanistic Aspects,* Chemical 2 Communications, Journal of the Chemical Society; No. 19; Oct. 1990.

Vaccher et al; *A Novel Rearrangement Reaction. A Single–step Conversion of Tetrahydro–1–isoquinolinecarboxylic Acids into 1–Isoquinolones [1],* Journal of Heterocyclic Chemistry; vol. 21, No. 3, pp. 1201–1204, Scheme 1, Compounds 2a–2c, May–Jun. 1984.

Yamato et al; *Reaction of 1,2,3, 4–Tetrahydroquinazolin–4–ones with Acid Anhydride. II Chemical & Pharmaceutical Bulletin;* vol. 29, No. 10; Oct. 1981.

Mori et al; *A Novel Synthesis Of Cyclic Imides And Quinolone By Use of Palladium Catalyzed Carbonylation,* Heterocycles; vol. 13 pp. 329–332; 30 Dec. 1979.

Chemical Abstracts; vol. 59, No. 3; 5 Aug. 1963.

Chemical Abstracts; vol. 63, No. 1; 5 Jul. 1965.

HETEROCYCLIC ALKANAMIDE

This is a division of parent application Ser. No. 08/262,892 filed Jun. 21, 1994 now U.S. Pat. No. 5,550,229.

The present invention relates to a novel process for preparing an azetidinone compound which is useful as a synthetic intermediate for a 1β-methylcarbapenem derivative having an antibacterial activity, and a novel starting compound therefor.

PRIOR ART

1β-Methylcarbapenem derivatives have been of great interests for their excellent antibacterial activities against a wide range of microorganisms including Gram positive and Gram negative bacteria, especially against Cephem-resistant bacteria, and their excellent stabilities in the human bodies.

Said 1β-methylcarbapenem derivatives have been synthesized by various processes up to now. In these processes, the azetidinone compound having a β-methyl group at the 1'-position of the 4-side chain of the formula:

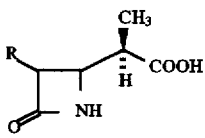

wherein R is a protected or unprotected hydroxy-substituted lower alkyl group, is especially important synthetic intermediate, which is prepared by removing 1'-hydrogen atom of the acetic acid moiety at the 4-position with a strong base, followed by introducing a methyl group to the product [cf. Heterocycles, 21, 29 (1984)].

However, it is difficult to stereoselectively obtain compounds having 1'-substituent with β-configuration of the 4-side chain by this process, and therefore, various processes for preparing stereoselectively the compound having 1'-substituent with β-configuration have been reported.

For example, Fuentes et al. suggest a process of reacting 4-acetoxy-azetidinone compound with a specific propionimide in the presence of a complex reagent of a specific base and a Lewis acid (e.g. tin triflate-ethylpiperidine-zinc bromide, diethylboran triflate-diisopropylethylamine-zinc bromide, etc.) (cf. L. M. Fuentes et al., J. Am. Chem. Soc., 108, 4675 (1986)). The similar process to Fuentes's is also reported by Nagao et al. (cf. Y. NAGAO et al., J. Am. Chem. Soc., 108, 4673 (1986)).

Besides, there is also reported a process of reacting 4-acetoxy-azetidinone compound with propionic acid thiol ester or propionic acid ester in the presence of a complex reagent of a base and a Lewis acid (cf. C. U. Kim et al., Tetrahedron Lett., 28, 507 (1987), A. Martel et al., Can. J. Chem., 66, 1537 (1988), and M. Endo, Can. J. Chem., 65, 2140 (1987)).

However, a complex reagent of a base and a Lewis acid is essential in these processes, and there are obtained as side-products undesirable compounds having the 1'-substituent with α-configuration, and hence, the yield and purity of the desired 1'-β-compound is insufficient.

BRIEF DESCRIPTION OF INVENTION

An object of the present invention is to provide a novel process for stereoselectively preparing azetidinone compound having the 1'-substituent with β-configuration which is useful as a synthetic intermediate for 1β-methylcarbapenem derivative having an antibacterial activity. Another object of the present invention is to provide a novel synthetic intermediate therefor.

DETAILED DESCRIPTION OF THE INVENTION

The present inventors have intensively studied a novel process for preparing a synthetic intermediate with desired 1'-β-configuration for carbapenem antibacterial agents without the defects of the conventional processes, and finally have found that the desired 1'-β-azetidinone compound is obtained by reacting an azetidinone compound having a leaving group with an alkanamide in the presence of a specific base without using a Lewis acid which is essential in the conventional processes.

That is, the present invention provides a novel process for preparing an azetidinone compound of the formula [III]:

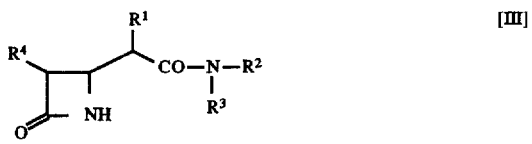

wherein $R^1$ is hydrogen atom or a lower alkyl group, $R^2$ and $R^3$ combine together with the adjacent nitrogen atom to form a heterocyclic group, and $R^4$ is a protected or unprotected hydroxy-substituted lower alkyl group, which comprises reacting an alkanamide of the formula [I]:

wherein $R^1$, $R^2$ and $R^3$ are the same as defined above, with a compound of the formula [II]:

wherein $L^1$ is a leaving group and $R^4$ is the same as defined above, in the presence of a base.

The present invention also provides a novel compound of the formula [I-A]:

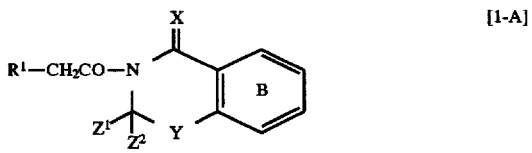

wherein Ring B is a substituted or unsubstituted benzene ring, X is oxygen atom or sulfur atom, Y is oxygen atom, sulfur atom, a protected or unprotected imino group or methylene group, $Z^1$ and $Z^2$ are the same or different and each hydrogen atom, a substituted or unsubstituted alkyl group, a substituted or unsubstituted cycloalkyl group, an aryl group or an aralkyl group, or both combine at the end thereof to form a substituted or unsubstituted alkylene group having 4 to 7 carbon atoms, and $R^1$ is the same as defined above, which is a starting compound for the compound [III].

The heterocyclic group of the formula $-N(R^2)(R^3)$ in the alkanamide of the formula [I] includes a 5- or 6-membered heterocyclic group having nitrogen atom or having oxygen atom or sulfur atom in addition to nitrogen atom, for example, groups disclosed in Japanese Patent First Publication (Kokai) Nos. 10765/1988, 252786/1987, 284176/1988, 29226911990, 788/1990, 275267/1986, 169781/1987, 77384/1987, 170377/1988, 246550/1987, 65195/1994, etc, i.e. groups of the formula:

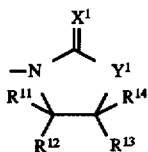

wherein $X^1$ is oxygen atom or sulfur atom, $Y^1$ is oxygen atom, sulfur atom, methylene group or imino group substituted by an alkyl group or an aryl group, $R^{11}$, $R^{12}$, $R^{13}$ and $R^{14}$ are the same or different and each hydrogen atom, a $C_1$-$C_5$ lower alkyl group, cyano group, an alkoxycarbonyl group, an aralkyl group, or an aryl group, or $R^{11}$ and $R^{12}$ combine together to form a $C_2$-$C_6$ alkylene chain, and simultaneously or independently $R^{13}$ and $R^{14}$ combine together to form a $C_2$-$C_6$ alkylene chain, or $R^{11}$, $R_{12}$, $R_{13}$ and $R^{14}$ combine together with the adjacent two carbon atoms to form a substituted or unsubstituted aromatic cyclic group.

The other examples of said heterocyclic groups are the groups disclosed in Japanese Patent Application Nos. 303662/1992, 111460/1993, 283148/1993, etc., i.e. groups of the formula:

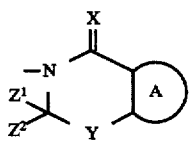

wherein X, Y, $Z^1$ and $Z^2$ are the same as defined above, Ring A is the same substituted or unsubstituted benzene ring as defined for Ring B, or a substituted or unsubstituted heterocyclic ring having 1 to 4 hetero atoms selected from oxygen atom, sulfur atom and nitrogen atom, or groups of the formula:

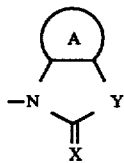

wherein X, Y and Ring A are the same as defined above.

Among the above mentioned heterocyclic rings, the suitable examples of Ring A are heterocyclic rings of the following formulae:

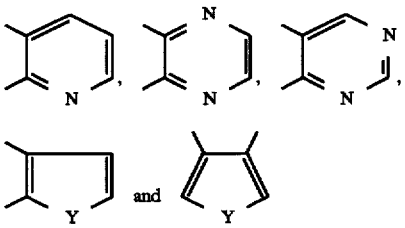

wherein Y is the same as defined above.

In the present invention, the substituents on Ring A and Ring B are preferably a halogen atom, a lower alkyl group, a lower alkoxy group, and an aryl group, and Ring A and Ring B may have one to four substituents which are the same or different. The group represented by $R^4$ is preferably a protected or unprotected 1-hydroxyethyl group, and the protecting group for said hydroxy group may be any ones which can easily be removed by a conventional method, for example, a lower alkoxycarbonyl group, a halogeno-lower alkoxycarbonyl group, a substituted or unsubstituted phenyl-lower alkyl group (e.g. benzyl group which may optionally be substituted by nitro group or a lower alkoxy group), a tri-lower alkylsilyl group, a substituted or unsubstituted phenyl-lower alkoxycarbonyl group (e.g. benzyloxycarbonyl group which may optionally be substituted by nitro group or a lower alkoxy group), and the like.

The alkyl group for $Z^1$, $Z^2$, $R^{11}$, $R^{12}$, $R^{13}$ and $R^{14}$ includes alkyl groups having 1 to 20 carbon atoms, preferably ones having 1 to 15 carbon atoms. The cycloalkyl group includes, for example, ones having 4 to 7 carbon atoms, and the aryl group includes, for example, a substituted or unsubstituted phenyl group. The aralkyl group includes, for example, a lower alkyl group substituted by a substituted or unsubstituted phenyl group. The substituents for alkyl group, cycloalkyl group, and the substituents on the phenyl group in the aryl group or in the aralkyl group are preferably a lower alkoxy group, a halogen atom, a protected or unprotected amino group.

The protecting group for amino group, or the protecting group for imino group represented by Y includes any group which is conventionally used as a protecting group in the field of Peptide Chemistry, and the examples of the protecting group are preferably a lower alkyl group, an acyl group (e.g. a lower alkanoyl group, a lower alkoxycarbonyl group, a substituted or unsubstituted phenylcarbonyl group, a substituted or unsubstituted phenyl-lower alkoxycarbonyl group).

Among the starting compounds [I], the compound of the formula [I-A] is a novel compound. The compound [I-A] of the present invention is structurally quite different from the above-mentioned known compound in that the amido moiety (hereinafter referred to as "supporting group") of the compound [I-A] of the present invention is the benzene ring-condensed 6-membered heterocyclic group, while the known supporting group is the 5-membered heterocyclic groups such as thiozolidine or oxazolidine. In the compound [I-A] of the present invention, any group having partial structure of the formula:

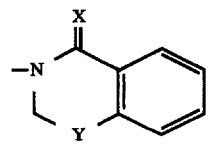

wherein the symbols are the same as defined above, can be used as the supporting group of the present invention, and therefore, when Ring B and/or Y have substituents, said substituents may be any one which does not disadvantageously affect the reaction. However, the compound [I-A] wherein Ring B is unsubstituted benzene ring, X and Y are both oxygen atom, $Z^1$ and $Z^2$ are a substituted or unsubstituted alkyl group, or both combine at the end thereof to form a unsubstituted alkylene group having 4 to 7 carbon atoms are more preferable.

The base used in the reaction of the alkanamide compound [I] and the compound [II] to give the compound [III] includes any conventional organic and inorganic bases, but strong bases are more preferable. The preferable strong base is a base having enough basicity to make an enolate by removing hydrogen atom at α-position of the alkanamide compound [I] and the more preferable base is a base having basicity of pKb<−10. Examples of a base include an alkali metal salt or alkaline earth metal salt of amines (e.g. alkali metal bis(tri-lower alkylsilyl)amide), or an alkali metal salt or alkaline earth metal salt of alcohols, more particularly lithium bis(trimethylsilyl)amide, sodium bis(trimethylsilyl)amide, potassium bis(trimethylsilyl)amide, lithium diisopropylamide, sodium amide, sodium methoxide, sodium ethoxide, potassium t-butoxide, and the like.

The reaction of the alkanamide compound [I] and the compound [II] is preferably carried out in an appropriate inert solvent such as ethers (e.g. tetrahydrofuran, diethyl ether, dioxane, dimethoxyethane, diisopropyl ether, etc.), aromatic hydrogen carbons (e.g. toluene, xylene, etc.), and the like, and more preferably carried out in tetrahydrofuran. The leaving group represented by $L^1$ in the compound [II] may be any conventional leaving groups which can easily be removed during the reaction with the alkanamide compound [I], for example, an acyloxy group, a lower alkylsulfonyloxy group, an arylsulfonyloxy group, a lower alkylsulfonyl group, an arylsulfonyl group, an arylthio group, a halogen atom, and the like, and an acyloxy group is more preferable.

The alkanamide compound [I] may be used in an amount of 1 to 1.5 moles, preferably 1.1 to 1.3 moles, per one mole of the compound [II]. The base may be used in an amount of 1 to 2 moles, preferable 1.2 to 1.5 moles, per one mole of the compound [II]. The reaction is usually carried out at a temperature of −80° C. to 10° C., preferably at −60° C. to −30° C.

The alkanamide compound [I] including the novel starting compound [I-A] is prepared by reacting a compound of the formula [IV]:

  [IV]

wherein $R^2$ and $R^3$ are the same as defined above, with a compound of the formula [V]:

  [V]

wherein $R^1$ is the same as defined above, or a reactive derivative thereof.

In preparing the novel starting compound [I-A] by the above reaction, a benzene compound of the formula [IV-1]:

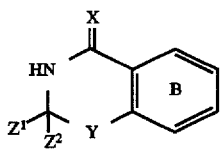  [IV-1]

wherein Ring B, X, Y, $Z^1$ and $Z^2$ are the same as defined above, is used as the compound [IV].

The reaction of the compound [IV] and the compound [V] is carried out in an appropriate solvent in the presence of a dehydrating agent. The dehydrating agent is preferably carbonyldiimidazole, dicyclohexylcarbodiimide, N-hydroxysuccinimide, 1-hydroxybenzotriazole, and the like, and the solvent is preferably ether, methylene chloride, tetrahydrofuran, acetonitrile, and the like. The reaction is carried out at a temperature of −30° C. to 70° C., preferably at 0° C. to 30° C.

The reaction of the compound [IV] and a reactive derivative of the compound [V] is carried out in an appropriate solvent in the presence or absence of an acid acceptor. The reactive derivative is preferably an acid halide or an acid anhydride of the compound [V]. The acid acceptor includes, for example, an alkali metal hydride, an alkali metal, or an organic base such as a lower alkyl lithium compound, an aryl lithium compound, pyridine, a di-lower alkyl-aniline, a tri-lower alkylamine, etc. The solvent is preferably tetrahydrofuran, diethyl ether, benzene, toluene, dichloromethane, chloroform, and the like. The reaction is carried out at a temperature of −80° C. to 50° C., preferably at a temperature of −20° C. to 30° C.

The azetidinone compound [III] prepared by the present process is converted into an azetidinonealkanoic acid of the formula [VI]:

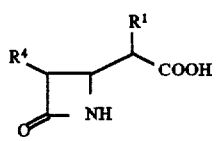  [VI]

wherein $R^1$ and $R^4$ are the same as defined above, by subjecting it to hydrolysis, which is a useful intermediate for carbapenem compounds.

The hydrolysis is carried out by a conventional method, but preferably in the presence of hydrogen peroxide and an alkali metal hydroxide in an appropriate solvent. The solvent includes, for example, a mixed solvent of an organic solvent (e.g. dioxane, tetrahydrofuran, dimethylformamide, methanol, etc.) and water, and the mixed solvent of tetrahydrofuran and water is more preferable. The alkali metal hydroxide includes, for example, lithium hydroxide, sodium hydroxide, potassium hydroxide, etc., and lithium hydroxide is more preferable. Besides, hydrogen peroxide may be used in an amount of 1 to 10 moles, preferably 6 to 8 moles, per one mole of the azetidinone compound [III]. The alkali metal hydroxide may be used in an amount of 1 to 5 moles, preferably 2 to 3 moles, per one mole of the azetidinone compound [III]. The reaction is carried out at a temperature of −10° C. to 30° C., preferably at −5° C. to 5° C.

The azetidinone compound [III] can be converted into the desired 1β-methylcarbapenem antibacterial agent. That is, the azetidinone compound [III] is reacted with an acetic acid compound of the formula [VII]:

  [VII]

wherein $R^5$ is hydrogen atom or an ester residue, and $L^2$ is a leaving group, to give an N-substituted azetidinone compound of the formula [VIII]:

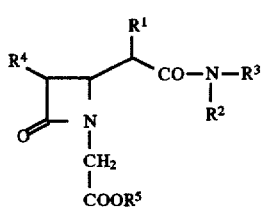  [VIII]

wherein $R^1, R^2, R^3, R^4$ and $R^5$ are the same as defined above, followed by subjecting the compound [VIII] or a salt thereof to intramolecular cyclization, esterifying the product to give a 1β-methyl-2-oxycarbapenem derivative of the formula [IX]:

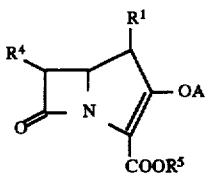

wherein a group of formula -OA is an esterified hydroxy group, and $R^1$, $R^4$ and $R^5$ are the same as defined above, reacting the compound [IX] with a thiol compound of the formula [X]:

wherein $R^6$ is an organic group, or a salt thereof, and when $R^4$ is a protected hydroxy-substituted lower alkyl group, and/or $R^5$ is an ester residue, if necessary, further by removing the protecting group for said hydroxy-substituted lower alkyl group and/or said ester residue to give a 1β-methyl-carbapenem derivative of the formula [XI]:

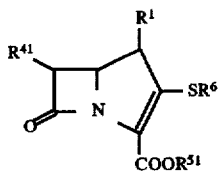

wherein $R^{41}$ is a protected or unprotected hydroxy-substituted lower alkyl group, $R^{51}$ is hydrogen atom or an ester residue, and $R^1$ and $R^6$ are the same as defined above.

The ester residue for $R^5$ in the acetic acid compound [VII], the N-substituted azetidinone compound [VIII] and the 1β-methyl-2-oxycarbapenem derivative [IX], and for $R^{51}$ in the 1β-methylcarbapenem derivative [XI] is, for example, an ester residue which may be metabolized or hydrolyzed in the human body, or an ester residue which can be a protecting group for carboxyl group.

The ester residue which may be metabolized or hydrolyzed in the human body includes, for example, groups of the formulae: -Q-OCOR$^7$, -Q-OCO$_2$R$^7$ or -Q-O-R$^7$ (wherein Q is a lower alkylene group, $R^7$ is a lower alkyl group, a cycloalkyl group, a lower alkenoyl group, a lower alkoxy-lower alkyl group, and a lower alkanoyloxy-lower alkyl group) such as a lower alkanoyloxy-lower alkyl group, a cycloalkylcarbonyloxy-lower alkyl group, a lower alkenoyloxy-lower alkyl group, a lower alkoxy-lower alkanoyloxy-lower alkyl group, a lower alkanoyloxy-lower alkoxy-lower alkyl group, a lower alkoxy-lower alkyl group, a lower alkoxy-lower alkoxy-lower alkyl group, a lower alkoxycarbonyloxy-lower alkyl group, a lower alkoxy-lower alkoxycarbonyloxy-lower alkyl group.

On the other hand, the ester residue which can be a protecting group for carboxyl group may be any ones which can easily be removed by a conventional method, for example, a lower alkyl group, a lower alkenyl group, a halogeno-lower alkyl group, a nitrobenzyl group, a lower alkoxy-benzyl group, and benzhydryl.

The esterified hydroxy group of the formula -OA includes, for example, a di-aryl-phosphoryloxy group or a di-lower alkylphosphoryloxy group of the formula -OP(O)(OR$^0$)$_2$ (wherein R$^0$ is an aryl group or a lower alkyl group), a substituted or unsubstituted lower alkylsulfonyloxyl group (e.g. methanesulfonyloxy group, ethanesulfonyloxy group, trifluoromethane-sulfonyloxy group, etc.), a substituted or unsubstituted arylsulfonyloxy group (e.g. benzenesulfonyloxy group, toluenesulfonyloxy group, etc.), a lower alkanoyloxy group (e.g. acetoxy group, etc.), an arylcarbonyloxy group (e.g. benzoyloxy group, etc.), and the like. Among these groups, the more preferable examples are active esterified hydroxy group such as a di-arylphosphoryloxy group, a di-lower alkylphosphoryloxy group, a substituted or unsubstituted lower alkylsulfonyloxy group, a substituted or unsubstituted arylsulfonyloxy group, and the like.

The organic group for $R^6$ in the thiol compound [X] and the 1β-methylcarbapenem derivative [XI] may be any groups which are used as a substituent for the conventional carbapenem antibacterial agents, for example, groups used for the carbapenem antibacterial agents disclosed in Japanese Patent First Publication (Kokai) Nos. 18779/1986, 202886/1985, 5081/1986, 49783/1990, 279588/1992, and U.S. Pat. No. 4,194,047. Examples of the organic group are a lower alkyl group, a cycloalkyl group, a 6- to 8-membered aryl group, a 4- to 8-membered aliphatic heterocyclic group, a 4- to 8-membered aromatic heterocyclic group, and the like. Moreover, these groups may have one or more substituents, and the substituent includes, for example, a lower alkyl group, hydroxy group, a lower alkoxy group, a lower alkylamino group, mercapto group, a lower alkylthio group, amidino group, guanidino group, carbamoyl group, thiocarbamoyl group, sulfamoyl group, cyano group, carboxyl group, a lower alkoxycarbonyl group, an aralkyloxycarbonyl group, oxo group, a halogeno group, a cycloalkyl group, a 6- to 8-membered aryl group, a 4- to 8-membered aliphatic heterocyclic group, a 4- to 8-membered aromatic heterocyclic group, and the like.

The reaction of the azetidinone compound [III] and the acetic acid compound [VII] is carried out in an appropriate solvent in the presence of a base. The leaving group for $L^2$ in the compound [VII] includes, for example, a halogen atom, an acyloxy group, and the like. The base includes, for example, an organic base such as 1,8-diazabicyclo[5.4.0]undec-7-en, etc., an alkali metal compound such as an alkali metal hydride, an alkali metal hydroxide, an alkali metal carbonate, and an alkali metal salt of amines such as sodium amide, lithium diisopropylamide, sodium bis(trimethylsilyl) amide, and the like. The solvent includes, for example, an inert solvent such as tetrahydrofuran, benzene, dichloromethane, etc. The reaction is carried out at a temperature of −50° C. to −20° C.

The intramolecular cyclization reaction of the N-substituted azetidinone compound [VIII] can be carried out in the presence of a base. The base includes, for example, an alkali metal salt of amines such as sodium bis(trimethylsilyl)amide, lithium bis(trimethylsilyl)amide, and an alkali metal salt of alcohols such as potassium t-butoxide, an alkali metal hydride such as sodium hydride, etc., and the like. The base may be used in an amount of 1.0 to 3.0 moles, preferably 2.0 to 2.5 moles, per one mole of the compound [VIII]. The solvent includes, for example, tetrahydrofuran, ethylene glycol dimethyl ether, dioxane, toluene, diethyl ether, benzene, etc. The reaction is carried out under cooling or at room temperature, for example, at a temperature of −78° C. to 50° C., preferably at a temperature of −60° C. to 10° C.

In the above intramolecular cyclization reaction of the compound [VIII], there is presumed to obtain an intramolecular cyclization product of the formula [XII]:

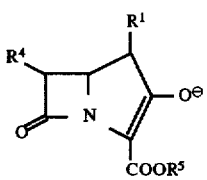

[XII]

wherein $R^1$, $R^4$ and $R^5$ are the same as defined above.

The compound [XII] thus obtained may be isolated from the reaction mixture or subjected to the subsequent esterification reaction without isolation. However, the intramolecular cyclization reaction and the subsequent esterification reaction may be preferably carried out in the same solvent without isolation of the compound [XII].

The esterification reaction of the compound [XII] can be carried out by reacting it with an esterifying reagent for hydroxy group. Examples of the esterifying reagent for hydroxy group are a reactive derivative (e.g. a corresponding acid halide, a corresponding acid anhydride) of phophoric acid compound or sulfuric acid compound such as a di-aryl phosphate (e.g. diphenyl phosphate, etc.), a di-lower alkyl phosphate (e.g. diethyl phosphate, etc.), a substituted or unsubstituted lower alkanesulfonic acid (e.g. methanesulfonic acid, ethanesulfonic acid, trifluoromethanesulfonic acid, etc.), a substituted or unsubstituted arylsulfonic acid (e.g. benzenesulfonic acid, toluenesulfonic acid, etc.), or a reactive derivative (e.g. a corresponding acid halide, a corresponding acid anhydride) of a lower alkanoic acid (e.g. acetic acid, etc.) or an arylcarboxylic acid (e.g. benzoic acid, etc.). The esterifying reagent for hydroxy group may be used in an amount of 1.0 to 4.0 moles, preferably 2.0 to 3.0 moles, per one mole of the compound [VIII].

Among them, the preferred esterifying reagents for hydroxy group are preferably an active esterifying reagent for hydroxy group such as a reactive derivative (e.g. a corresponding acid halide, a corresponding acid anhydride) of phosphoric acid compound or sulfuric acid compound, for example, a reactive derivative (e.g. a corresponding acid halide, a corresponding acid anhydride) of a di-aryl phosphate, a di-lower alkyl phosphate, a substituted or unsubstituted lower alkanesulfuric acid, a substituted or unsubstituted arylsulfonic acid. The reaction is carried out under cooling or at room temperature, preferably at a temperature of −75° C. to 40° C., more preferably at a temperature of −60° C. to 10° C.

The intramolecular cyclization reaction of the compound [VIII] and the subsequent esterification reaction are carried out in the presence or absence of an acid, but it is preferable to carry out these reactions in the presence of an acid.

The acid may be either a Lewis acid or protonic acid, but Lewis acids are more preferable. The Lewis acid includes, for example, a metal halide such as cupric chloride, cuprous iodide, zinc chloride, zinc iodide, zinc fluoride, ferric chloride, stannous chloride, stannic chloride, etc., and boron compounds such as trimethyl borate, etc., or a silyl compound such as tri-lower alkyl-halogenosilane (e.g. trimethylchlorosilane, t-butyldimethylchlorosilane, etc.), a tetrahalogenosilane (e.g. tetrachlorosilane, etc.). The Lewis acid may be used in an amount of 0.1 to 2.0 moles, preferably 1.0 to 1.5 moles, per one mole of the compound [VIII].

The protonic acid includes, for example, sulfuric acid, p-toluene-sulfonic acid, acetic acid, citric acid, hydrochloric acid, phosphoric acid, boric acid, etc., and may be used in an amount of 0.1 to 1.0 mole per one mole of the compound [VIII].

When the above esterification reaction is carried out in the presence of an acid, the esterifying reagent may be used in an amount of 1.2 to 1.5 moles per one mole of the compound [VIII].

The reaction of the 1β-methyl-2-oxycarbapenem derivative [IX] and the thiol compound [X] is carried out according to the method disclosed in Japanese Patent First Publication (Kokai) No. 279588/1992. When $R^4$ is a protected hydroxy-substituted lower alkyl group, and/or $R^5$ is an ester residue, the protecting group for said hydroxy group and/or the ester residue may be removed by a conventional method, for example, hydrolysis, reduction, etc., if necessary.

In the above reactions, the compounds [VIII], [IX] and [X] may be used in the form of a salt thereof as well. The salts of these compounds [VIII], [IX] and [X] are, for example, an alkali metal salt, a tri-lower alkylammonium salt, etc.

Since the present process proceeds with keeping the stereo-structure of the compound [III], the compound [III] can be converted into the 1β-methyl-2-oxycarbapenem derivative [IX] and the 1β-methylcarbapenem derivative [XI] without epimerization.

Besides, the compound [IV] can be prepared by a conventional method. Among them, the benzene compound of the formula[IV-2]:

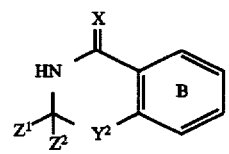

[IV-2]

wherein $Y^2$ is oxygen atom, sulfur atom or an imino group which may have substituent(s), and Ring B, X, $Z^1$ and $Z^2$ are the same as defined above, is prepared by the method disclosed in Journal of the American Chemical Society, 72, 721 (1950). That is, the compound [IV-2] is prepared by condensing a compound of the formula [XIII]:

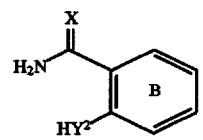

[XIII]

wherein Ring B, X and $Y^2$ are the same as defined above, with a compound of the formula [XIV]:

[XIV]

wherein $Z^1$ and $Z^2$ are the same as defined above, in the presence of an acid (e.g. p-toluenesulfonic acid, sulfuric acid, hydrochloric acid, etc.).

Besides, the compound [XIII] in which X is oxygen atom and $Y^2$ is sulfur atom may be prepared by halogenating a compound of the formula [XV]:

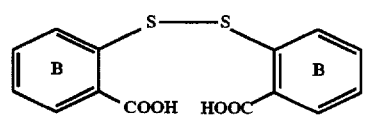

[XV]

wherein Ring B is the same as defined above, to give a compound of the formula [XVI]:

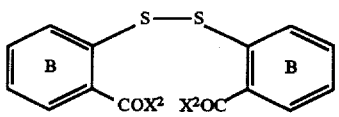

wherein X² is a halogen atom, and Ring B is the same as defined above, subjecting the compound [XVI] to amidation to give a compound of the formula [XVII]:

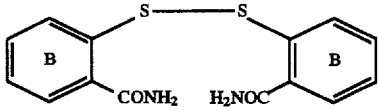

wherein Ring B is the same as defined above, and then reducing the compound [XVII].

Besides, the compound [XIII] in which X is oxygen atom and Y² is an imino group which may have substituents(s) may be prepared by reacting a compound of the formula [XVIII]:

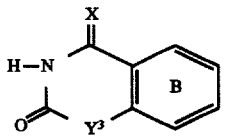

wherein Y³ is an imino group which may have substituent (s), and other symbols are the same as defined above, with ammonia.

Besides, the compound [XIII] in which X is sulfur atom and Y² is sulfur atom or an imino group which may have substituent(s) may be prepared by subjecting the compound [XIII] in which X is oxygen atom and Y² is sulfur atom or an imino group which may have substituent(s) to thiocarbonylation.

Besides, the benzene compound [IV-1] in which Y is methylene group may be prepared by reacting the compound of the formula:

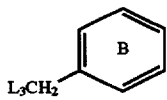

wherein L³ is a halogen atom or hydroxy group, and Ring B is the same as defined above, with a compound of the formula:

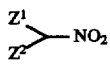

wherein Z¹ and Z² are the same as defined above, to give a compound of the formula:

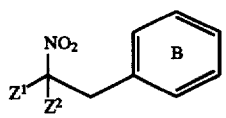

wherein the symbols are the same as defined above, reducing the compound to give a compound of the formula:

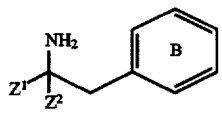

wherein the symbols are the same as defined above, reacting the compound with a compound of the formula:

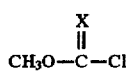

wherein X is the same as defined above, and then subjecting the product to intramolecular cyclization.

Throughout the present specification and claims, the lower alkyl group, the lower alkylene group and the lower alkoxy group are preferably a straight chain or branched chain alkyl group, alkoxy group and alkylene group having 1 to 6 carbon atoms, preferably 1 to 4 carbon atoms, respectively. The lower alkanoyl group and the lower alkenyl group are ones having 2 to 8 carbon atoms, preferably 2 to 6 carbon atoms, respectively. The lower alkenoyl group and the cycloalkyl group are ones having 3 to 8 carbon atoms, preferably 3 to 6 carbon atoms, respectively.

EXAMPLES

The present invention is illustrated in more detail by the following Examples and Reference Example, but should not be construed to be limited thereto.

Example 1

To a solution of 2,2-di-n-butyl-2,3-dihydro-4H-1,3-benzoxadin-4-one (13.5 g, 51.7 mmole) in methylene chloride (30 ml) are added dropwise a solution of propionyl bromide (6.05 ml, 67.2 mmole) in methylene chloride (15 ml) and a solution of pyridine (5.02 ml, 62.0 mmole) in methylene chloride (15 ml) at −20° C. under nitrogen atmosphere over a period of about 30 minutes. After the addition, the reaction mixture is warmed gradually, and stirred at room temperature overnight. To the reaction mixture is added water (50 ml), and the mixture is separated. The aqueous layer is extracted with methylene chloride (50 ml), and the organic layers are combined, and washed successively with saturated sodium hydrogen carbonate solution and saturated saline solution, dried over anhydrous magnesium sulfate, and concentrated under reduced pressure. The residue is purified by silica gel column chromatography (solvent; hexane/ethyl acetate=19:1) to give 2,2-di-n-butyl-3-propionyl-2,3-dihydro-4H-1,3-benzoxadin-4-one (14.8 g).

Yield; 90%

M.p. 52°–54° C.

NMR δ (CDCl₃): 0.65 (6H, t, J=5.0 Hz), 1.03–1.62 (11H, m), 1.94–2.44 (4H, m), 2.91 (2H, q, J=7.2 Hz), 6.91 (1H, d, J=8.0 Hz), 7.07 (1H, dd, J=7.8, 7.8 Hz), 7.50 (1H, ddd, J=1.6, 8.0, 8.0 Hz), 7.94 (1H, dd, J=1.6, 8.0 Hz), IR (KBr) cm⁻¹: 1718, 1682, 1610, 1469, 1174

Example 2

Using solutions of spiro[2,3-dihydro-4H-1,3-benzoxadine-2,1'-cyclohexan]-4-one (30.0 g, 138 mmole) in methylene chloride (60 ml), propionyl bromide (16.1 ml, 179 mmole)in methylene chloride (30 ml) and pyridine (13.4 ml, 166 mmole) in methylene chloride (30 ml), 3-propionyl-spiro[2,3-dihydro-4H-1,3-benzoxadine-2,1'- cyclohexan]-4-one (34.7 g) is obtained in the same manner as in Example 1.

Yield; 92%

M.p. 58°–60° C.

NMR δ (CDCl₃): 1.20 (3H, t, J=7.4 Hz), 1.16–1.43 (2H, m), 1.55–1.81 (4H, m), 1.98–2.40 (4H, m), 2.84 (2H, q, J=7.4 Hz), 6.98 (1H, d, J=8.2 Hz), 7.10 (1H, dd, J=7.6, 7.6 Hz), 7.52 (1H, ddd, J=1.6, 7.6, 7.6 Hz), 7.95 (1H, dd, J=1.6, 8.2 Hz) IR (KBr) cm⁻¹: 1724, 1687, 1611, 1467, 1320, 1159

Example 3

To a solution of 2,2-di-n-butyl-3-propionyl-2,3-dihydro-4H-1,3-benzoxadin-4-one (190 mg, 0.6 mmole) in tetrahydrofuran (3 ml) is added dropwise 1M solution (0.7 ml) of sodium bis(trimethyisilyl)amide in tetrahydrofuran at -60° C. under nitrogen atmosphere, and the mixture is stirred at the same temperature for one hour. To the mixture is added dropwise (3R,4R)-4-acetoxy-3-[(1R)-1-t-butyldimethylsilyloxyethyl]-2-azetidinone (143 mg, 0.5 mmole) in tetrahydrofuran (1 ml) at -50° C., and the mixture is stirred for 10 minutes. To the reaction solution is added 0.1M phosphate buffer (pH 7.0, 10 ml), and the mixture is extracted with ethyl acetate (10 ml). The buffer layer is extracted with ethyl acetate (5 ml), and the organic layers are combined, washed with water, dried over anhydrous magnesium sulfate, and concentrated under reduced pressure. The residue is purified by silica gel column chromatography (solvent; hexane/ethyl acetate=20:1 to 4:1) to give 3-{(2R)-2-[(3S,4R)-3-[(1R)-1-t-butyldimethylsilyloxyethyl]-2-oxoazetidin-4-yl]-propionyl}-2,2-di-n-butyl-2,3-dihydro-4H-1,3-benzoxadin-4-one (237 mg).

Yield; 87%

M.p. 100°–102° C.

β:α=100:0 (HPLC)

NMR δ (CDCl₃): 0.07 (9H, s), 0.78–1.02 (12H, m), 1.10–1.58 (11H, m), 1.92–2.44 (4H, m), 3.13–3.20 (1H, m), 3.70–3.82 (1H, m), 4.07–4.24 (2H, m), 5.97 (1H, s), 6.92 (1H, d, J=8.1 Hz), 7.09 (1H, dd, J=7.4, 7.4 Hz), 7.53 (1H, ddd, J=1.6, 8.1, 8.1 Hz), 7.93 (1H, dd, J=1.6, 7.4 Hz)

Example 4

3-Propionyl-spiro[2,3-dihydro-4H-1,3-benzoxadine-2,1'-cyclohexan]-4-one (164 mg, 0.6 mmole) is reacted with (3R,4R)-4-acetoxy-3-[(1R)-1-t-butyldimethylsilyloxyethyl]-2-azetidinone (143 mg, 0.5 mmole) in the same manner as Example 3 to give 3-{(2R)-2-[(3S,4R)-3-[(1R)-1-t-butyldimethylsilyl-oxyethyl]-2-oxoazetidin-4-yl]propionyl}-spiro[2,3-dihydro-4H-1,3-benzoxadin- 2,1'-cyclohexan]-4-one (205 mg).

Yield; 82%

M.p. 149°–151° C.

β:α=100:0 (HPLC)

NMR δ (CDCl₃): 0.07 (9H, s), 0.85 (6H, s), 1.16–1.40 (5H, m), 1.50–2.40 (8H, m), 3.16–3.24 (1H, m), 3.48–3.63 (1H, m), 4.00–4.30 (2H, m), 5.95 (1H, s), 7.00 (1H, d, J=8.2 Hz), 7.11 (1H, dd, J=7.5, 7.5 Hz), 7.54 (1H, ddd, J=1.6, 7.5, 7.5 Hz), 7.93 (1H, dd, J=1.6, 8.2 Hz)

EXAMPLE 5

Using lithium bis(trimethylsilyl)amide instead of sodium bis(trimethylsilyl)amide, 3-{(2R)-2-[(3S,4R)-3-[(1R)-1-t-butyldimethylsilyloxyethyl]-2-oxoazetidin-4-yl]propionyl}-2,2-di-n-butyl-2,3-dihydro-4H-1,3-benzoxadin-4-one is obtained in the same manner as in Example 3.

β:α=100:0. (HPLC)

Example 6

Using lithium bis(trimethylsilyl)amide, 3-{(2R)-2-[(3S, 4R)-3-[(1R)-1-t-butyldimethylsilyloxyethyl]-2-oxoazetidin-4-yl]propionyl}-spiro[2,3-dihydro-4H-1,3-benzoxadin-2,1'-cyclohexan]-4-one is obtained in the same manner as in Example 4.

β:α=100:0 (HPLC)

Examples 7 to 18

The corresponding starting compounds and propionyl chloride are treated in the same manner as in Example 1 to give the compounds listed in Table 1.

TABLE 1

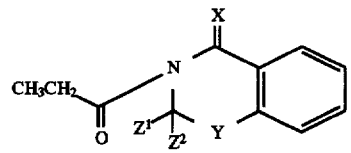

| Ex. No. | X | Y | Z¹ | Z² | M.p. (°C.) |
|---|---|---|---|---|---|
| 7 | O | O | CH₃ | CH₃ | 26–27 |
| 8 | O | O | C₂H₅ | C₂H₅ | 47–49 |
| 9 | O | O | C₁₅H₃₁ | C₁₅H₃₁ | 68–71 |
| 10 | O | O | PhCH₂ | PhCH₂ | 76–77 |
| 11 | S | O | —(CH₂)₅— | | 102–104 |
| 12 | S | O | CH₃ | CH₃ | 46–48 |
| 13 | O | S | —(CH₂)₅— | | 101–102 |
| 14 | O | CH₂ | H | H | 82–83 |
| 15 | O | NCH₃ | CH₃ | CH₃ | 58–60 |
| 16 | O | O | (CH₃)₂CH | (CH₃)₂CH | Oil* |
| 17 | O | O | C₃H₇ | C₃H₇ | 41–42 |
| 18 | O | O | C₆H₅ | C₆H₅ | 197–200 |

*: B.p. 145–150° C. (1–2 mmHg)

Examples 19 to 46

The corresponding starting compounds and propionyl bromide are treated in the same manner as in Example 1 to give the compounds listed in Tables 2 and 3.

TABLE 2

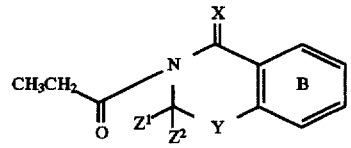

| Ex. No. | X | Y | Z¹ | Z² | Ring B |
|---|---|---|---|---|---|
| 19 | O | O | CH₃ | CH₃ | |
| 20 | O | O | C₁₅H₃₁ | C₁₅H₃₁ | |
| 21 | O | O | PhCH₂ | PhCH₂ | |
| 22 | O | O | —(CH₂)₄— | | |

TABLE 2-continued

![Structure: CH3CH2-C(=O)-N(-)-C(Z1)(Z2)-Y-Ring B with C=X]

| Ex. No. | X | Y | Z¹ | Z² | Ring B |
|---------|---|---|-----|-----|--------|
| 23 | O | S | C₄H₉ | C₄H₉ | phenyl |
| 24 | O | NCH₃ | —(CH₂)₅— | | phenyl |
| 25 | S | O | C₄H₉ | C₄H₉ | phenyl |
| 26 | S | S | —(CH₂)₅— | | phenyl |
| 27 | S | NCH₃ | PhCH₂ | PhCH₂ | phenyl |
| 28 | O | CH₂ | CH₃ | CH₃ | phenyl-OCH₃ |
| 29 | O | O | —(CH₂)₅— | | phenyl-Cl |
| 30 | O | O | —(CH₂)₅— | | phenyl-CH₃ |
| 31 | O | O | —(CH₂)₅— | | phenyl-OCH₃ |
| 32 | S | S | CH₃ | CH₃ | phenyl |
| 33 | S | S | —(CH₂)₄— | | phenyl |
| 34 | O | NCH₃ | C₄H₉ | C₄H₉ | phenyl |
| 35 | O | —CH₂— | —(CH₂)₅— | | phenyl |
| 36 | O | O | —(CH₂)₄— | | phenyl |
| 37 | O | S | C₄H₉ | C₄H₉ | phenyl |
| 38 | S | O | C₄H₉ | C₄H₉ | phenyl |

TABLE 3

![Structure: CH3CH2-C(=O)-N(-)-C(R12)(R22)-C(=X1)-Y1]

| Ex. No. | X¹ | Y¹ | R¹² | R²² |
|---------|-----|-----|-----|-----|
| 39 | O | O | (CH₃)₂CH | H |
| 40 | S | O | (CH₃)₂CH | H |
| 41 | O | S | CH₃ | CH₃ |
| 42 | S | S | (CH₃)₂CH | H |
| 43 | O | NCH₃ | CH₃ | CH₃ |
| 44 | O | O | CH₃ | CH₃ |
| 45 | S | S | CH₃ | CH₃ |
| 46 | O | O | (CH₃)₂CH | H |

Examples 47 to 66

The corresponding starting compounds and (3R,4R)-4-acetoxy-3-[(1R)-1-t-butyldimethylsilyloxyethyl]-2-azetidinone are treated in the same manner as in Example 3 to give the compounds listed in Tables 4 and 5.

TABLE 4

| Ex. No. | X | Y | $Z^1$ | $Z^2$ | M.p. (°C.) | β/α | Ring B |
|---|---|---|---|---|---|---|---|
| 47 | O | O | $CH_3$ | $CH_3$ | 131–133 | 99/1 | |
| 48 | O | O | $C_{15}H_{31}$ | $C_{15}H_{31}$ | Oil | 99/1 | |
| 49 | O | O | $PhCH_2$ | $PhCH_2$ | Caramel | | |
| 50 | O | O | $C_2H_5$ | $C_2H_5$ | 181–183 | 100/0 | |
| 51 | S | O | —$(CH_2)_5$— | | 143–144 | 100/0 | |
| 52 | S | O | $CH_3$ | $CH_3$ | 146–148 | 100/0 | |
| 53 | O | S | —$(CH_2)_5$— | | 147–150 | 96/4 | |
| 54 | O | $CH_2$ | H | H | 143–146 | 93/7 | |
| 55 | O | $NCH_3$ | $CH_3$ | $CH_3$ | 141–144 | | |
| 56 | O | O | $(CH_3)_2CH$ | $(CH_3)_2CH$ | 119–120 | 100/0 | |
| 57 | O | O | $C_3H_7$ | $C_3H_7$ | 185–187 | 100/0 | |
| 58 | O | O | $C_6H_5$ | $C_6H_5$ | Syrup | 94/6 | |
| 59 | O | $CH_2$ | $CH_3$ | $CH_3$ | Syrup | | $OCH_3$ substituted |

TABLE 4-continued

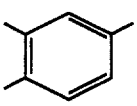

| Ex. No. | X | Y | Z¹ | Z² | M.p. (°C.) | β/α | Ring B |
|---|---|---|---|---|---|---|---|
| 60 | O | O |   | —(CH$_2$)$_5$— | Syrup | | 2,3-di-substituted with Cl |
| 61 | O | O |   | —(CH$_2$)$_5$— | 173–175 | | 2,3-di-substituted with CH$_3$ |
| 62 | O | O |   | —(CH$_2$)$_5$— | 155–158 | | 2,3-di-substituted with OCH$_3$ |

TBS: t-Butyldimethylsilyl group

TABLE 5

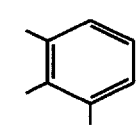

| Ex. No. | X¹ | Y¹ | R¹² | R²² | IRν$_{max}$ (cm$^{-1}$) | β/α |
|---|---|---|---|---|---|---|
| 63 | O | O | (CH$_3$)$_2$CH | H | 1697, 1778, 3330 | 100/0 |
| 64* | O | O | CH$_3$ | CH$_3$ | 1706, 1762, 3200 | 70/30 |
| 65* | S | S | CH$_3$ | CH$_3$ | 1772, 1761, 3180 |  |
| 66* | O | O | (CH$_3$)$_2$CH | H |  | 100/0 |

TBS: t-Butyldimethylsilyl group
*): Lithium bis(trimethylsilyl)amide is used instead of sodium bis(trimethylsilyl)amide.

Examples 67 to 80

The corresponding starting compounds and (3R,4R)-4-acetoxy-3-[(1R)-1-t-butyldimethylsilyloxyethyl]-2-azetidinone are treated in the same manner as in Example 3 to give the compounds listed in Tables 6 and 7.

TABLE 6

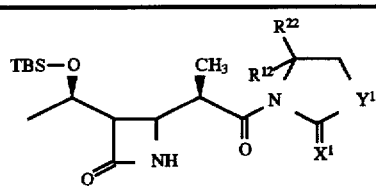

| Ex. No. | X | Y | Z¹ | Z² |
|---|---|---|---|---|
| 67 | O | O |   | —(CH$_2$)$_4$— |
| 68 | O | S | C$_4$H$_9$ | C$_4$H$_9$ |

TABLE 6-continued

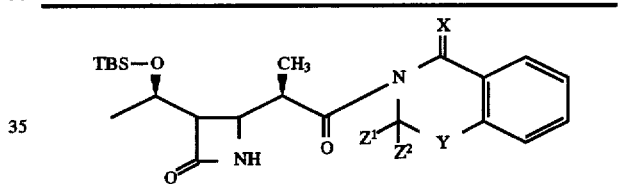

| Ex. No. | X | Y | Z¹ | Z² |
|---|---|---|---|---|
| 69 | O | NCH$_3$ |   | —(CH$_2$)$_5$— |
| 70 | S | O | C$_4$H$_9$ | C$_4$H$_9$ |
| 71 | S | S |   | —(CH$_2$)$_5$— |
| 72 | S | NCH$_3$ | PhCH$_2$ | PhCH$_2$ |
| 73 | S | S | CH$_3$ | CH$_3$ |
| 74 | S | S |   | —(CH$_2$)$_4$— |
| 75 | O | NCH$_3$ | n-C$_4$H$_9$ | n-C$_4$H$_9$ |
| 76 | O | —CH$_2$— |   | —(CH$_2$)$_5$— |

TBS: t-Butyldimethylsilyl group

TABLE 7

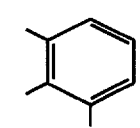

| Ex. No. | X¹ | Y¹ | R¹² | R²² |
|---|---|---|---|---|
| 77 | S | O | (CH$_3$)$_2$CH | H |
| 78 | O | S | CH$_3$ | CH$_3$ |
| 79 | S | S | (CH$_3$)$_2$CH | H |
| 80 | O | NCH$_3$ | CH$_3$ | CH$_3$ |

TBS: t-Butyldimethylsilyl group

Example 81

Using sodium methylate, 3-{(2R)-2-[(3S,4R)-3-[(1R)-1-t-butyldimethylsilyloxyethyl]-2-oxoazetidin-4-yl]

propionyl}-2,2-di-n-butyl-2,3-dihydro-4H-1,3-benzoxadin-4-one is obtained in the same manner as in Example 3.

Example 82

(A) To a solution of 3-{(2R)-2-[(3S,4R)-3-[(1R)-1-t-butyldimethylsilyloxyethyl]-2-oxoazetidin-4-yl]propionyl}-spiro[2,3-dihydro-4H-1,3-benzoxadine-2,1'-cyclohexan]-4-one (7 g) and bromoacetic acid allyl ester (2.89 g) in tetrahydrofuran (35 ml) is added 1M sodium bis (trimethylsilyl)amido•tetrahydrofuran solution (16.2 ml) at −60° C., and the mixture is warmed to −30° C. over one hour. The reaction solution is poured into a mixture of water-ethyl acetate, and the ethyl acetate layer is washed, dried, and evaporated to remove the solvent. The residue is purified by silica gel column chromatography (solvent; hexane/ethyl acetate=20:1 to 5:1) to give 3-{(2R)-2-[(3S,4R)-1-allyloxycarbonylmethyl-3-[(1R)-1-t-butyldimethylsilyloxyethyl]-2-oxoazetidin-4-yl]propionyl}-spiro[2,3-dihydro-4H-1,3-benzoxadine-2,1'-cyclohexan]-4-one (8.03 g) as syrup.

(B) A solution of 3-{(2R)-2-[(3S,4R)-1-allyloxycarbonylmethyl-3-[(1R)-1-t-butyldimethylsilyloxyoxyethyl]-2-oxoazetidin-4-yl]propionyl}-spiro[2,3-dihydro-4H-1,3-benzoxadine-2,1'-cyclohexan]-4-one (1.2 g) in tetrahydrofuran (6 ml) is added dropwise to 1M sodium bis(trimethylsilyl)amide•tetrahydrofuran solution (4.4 ml) at a temperature of −30° C. to −20° C. over one minute. To the mixture is added trimethylsilyl chloride (261 mg) at −50° C., and the mixture is stirred for two minutes. To the mixture is added diphenylphosphoryl chloride (645 mg) at −50° C., and the mixture is stirred at 0° C. for two hours. The reaction solution is poured into 0.2M phosphate buffer (pH 7.0, 50 ml), and the mixture is extracted with ethyl acetate. The extract is washed, dried, and evaporated to remove the solvent. To the residue is added isopropyl ether, and the mixture is filtered to collect spiro[2,3-dihydro-4H-1,3-benzoxadin-2,1'-cyclohexan]-4-one (355 mg) as precipitates. The filtrate is concentrated to give (1R,5R,6S)-6-[(1R)-1-t-butyldimethylsilyloxyethyl]-1-methyl-2-diphenylphosphoryloxy-carbapen-2-em-3-carboxylic acid allyl ester (1.04 g) as syrup.

Example 83

To a solution of 3-{(2R)-2-[(3S,4R)-3-[(1R)-1-t-butyldimethylsilyloxyethyl]-2-oxoazetidin-4-yl]propionyl}-spiro[2,3-dihydro-4H-1,3-benzoxadin-2,1'-cyclohexan]-4-one (500 mg) in tetrahydrofuran/water (20 ml) are added successively 30% aqueous hydrogen peroxide solution (0.9 ml) and lithium hydroxide (84 mg) at 0° C., and the mixture is stirred at the same temperature for one hour. To the mixture is added dropwise 1.5N aqueous sodium sulfite solution (5 ml) at the same temperature to adjust the pH value of the mixture to about pH 10. The mixture is evaporated under reduced pressure to remove the tetrahydrofuran. The precipitated crystals are removed by filtration, and the aqueous filtrate is washed with chloroform (20 ml), and thereto is added 10% hydrochloric acid (10 ml) to adjust the pH value of the mixture to about pH 1. The aqueous layer is extracted with ethyl acetate (30 ml), and the organic layer is dried, concentrated under reduced pressure, and recrystallized from a mixture of ethyl acetate/hexane to give (2R)-2-[(3S,4R)-3-[(1R)-1-t-butyldimethylsilyloxyethyl]-2-oxoazetidin-4-yl]propionic acid (216 mg).

M.p. 146°–147° C.

Reference Example 1

Dibutyl ketone (20 g), salicylamide (19.3 g) and p-toluenesulfonic acid hydrate (2.7 g) are added to toluene (300 ml), and the mixture is refluxed overnight during which the water is removed by Dean-Stark apparatus. After cooling, the reaction solution is washed, dried, and evaporated to remove the solvent. The residue is purified by silica gel column chromatography (solvent; hexane/ethyl acetate= 95:5) to give 2,2-dibutyl-4-oxo-2,3-dihydro-4H-1,3-benzoxadine (34 g) as yellow oil.

Reference Example 2

(1) Thionyl chloride (12.5 ml) is added dropwise to a solution of 2,2'-dithiodibenzoic acid (25.0 g) in a mixture of toluene (120 ml) and dimethylformamide (0.5 ml) at room temperature. The mixture is warmed to a temperature of 70° to 80° C. and then stirred at the same temperature overnight. After 20 hours, the crystals are collected by filtration to give 2,2'-dithiodibenzoyl chloride (14.9 g) as colorless crystal.

M.p. 140°–141° C.

(2) Aqueous ammonia (20 ml) is added to a suspension of 2,2'-dithiodibenzoyl chloride (7.03 g) in dioxane (20 ml) at room temperature. The mixture is warmed to a temperature of 80° to 90° C. and stirred for five hours at the same temperature. The mixture is cooled to room temperature to give 2,2'-dithiodibenzoylamide (4.8 g) as colorless crystal.

M.p. 249°–250° C.

(3) 2N Hydrochloric acid (41 ml) is added dropwise to a suspension of 2,2'-dithiodibenzoylamide (4.14 g) and zinc powders (2.5 g) in dioxane (70 ml). The mixture is warmed to a temperature of 60° to 70° C. and stirred for four hours at the same temperature. The reaction mixture is poured into water (50 ml), and the mixture is extracted with ethyl acetate. The ethyl acetate layer is washed, dried and evaporated under reduced pressure to remove the solvent. A mixture of cyclohexanone (5.64 ml) and p-toluenesulfonic acid monohydrate (1.03 g) is added to a solution of the above obtained residue in toluene, and the mixture is refluxed for 40 minutes by making use of a dehydrator of Dean Stark. After cooling to room temperature, the reaction mixture is condensed under reduced pressure and methanol is added thereto. The precipitates are collected by filtration to give spiro[2,3-dihydro-4H-1,3-benzothiazine-2,1'-cyclohexan]-4-one (3.05 g) as colorless crystal.

M.p. 193°–195° C.

Reference Example 3

(1) N-Methylisatic acid (10.0 g) is added gradually to water (140 ml) at room temperature and thereto is added dropwise aqueous ammonia (9.6 g). The mixture is warmed to 80° C. during 45 minutes, and ethanol is added thereto until the reaction mixture becomes colorless. Then, the reaction mixture is cooled to room temperature and the precipitated crystals are collected by filtration to give 2-carbamoyl-N-methylaniline (7.11 g) as colorless crystal.

M.p. 155°–156° C.

(2) A mixture of cyclohexanone (6.9 ml) and p-toluenesulfonic acid monohydrate (633 mg) is added to a solution of the above obtained product (5.00 g) in toluene, and the mixture is refluxed with dehydration by making use of a dehydrator of Dean Stark for one hour. After cooling to room temperature, the precipitated crystals are collected by filtration and washed with methanol to give spiro[1-methyl-1,2,3,4-tetrahydroquinazoline-2,1'-cyclohexan]-4-one (6.32 g) as colorless crystal.

M.p. 183°–185° C.

Reference Example 4

(1) A solution of ethoxycarbonyl chloride (9.6 g) in ether (25 ml) is added dropwise to a solution of 1-(2-amino-2- methylpropyl)-4-methoxybenzene (30 g) in ether (300 ml) under ice-cooling. Then, a solution of ethoxycarbonyl chloride (9.6 g) in ether (25 ml) and a solution of sodium hydroxide (8 g) in water (50 ml) are added dropwise thereto. After addition, the mixture is stirred for one hour, and water is added thereto. The ether layer is removed therefrom and the aqueous layer is extracted with ether twice. A mixture of the ether layer and the extract is dried and evaporated to remove the solvent. The residue is purified by column chromatography to give 1-[2-(N-ethoxycarbonyl)amino-2-methylpropyl]-4-methoxybenzene (29.1 g) as an oil.

NMR (CDCl$_3$) δ 1.02 (6H, s), 1.32 (3H, t, J=7.5 Hz), 3.12 (2H, s), 3.72 (3H, s), 4.17 (2H, q, J=7.5 Hz), 6.70–7.10 (4H, m) (2) The above product (10 g) is added to polyphosphoric acid (100 ml) and the mixture is stirred at room temperature for 30 minutes. Then, the mixture is gradually warmed to a temperature of 100° C. and stirred at the same temperature for two hours. After cooling to room temperature, water (300 ml) is added thereto and the mixture is extracted with chloroform. The extract is dried and evaporated to remove the solvent. The residue is purified by column chromatography to give 1-oxo-3,3-dimethyl-7-methoxy-1,2,3,4-tetrahydroisoquinoline (5.43 g) as an oil.

NMR (CDCl$_3$) δ 1.02 (6H, s), 3.10 (2H, s), 3.72 (3H, s), 6.90 (1H, d, J=9 Hz), 7.45 (1H, dd, J=3 Hz, 9 Hz), 7.85 (1H, d, J=3 Hz)

Reference Examples 5 to 14

The corresponding starting compounds [XII] and the corresponding starting compounds [XIV] are treated in the same manner as in Reference Example 1 to give the compounds listed in Table 8.

TABLE 8

| Ref. Ex. No. | Z$^1$ | Z$^2$ | Ring B | Y | M.p. (°C.) |
|---|---|---|---|---|---|
| 5 | n-C$_{15}$H$_{31}$ | n-C$_{15}$H$_{31}$ | phenyl | O | Yellow Oil |
| 6 | —CH$_2$—phenyl | —CH$_2$—phenyl | phenyl | O | 159–161 |
| 7 | —(CH$_2$)$_5$— | | Cl-substituted phenyl | O | 168–170 |
| 8 | —(CH$_2$)$_5$— | | CH$_3$-substituted phenyl | O | 175–177 |
| 9 | —(CH$_2$)$_5$— | | OCH$_3$-substituted phenyl | O | 193–195 |
| 10 | (CH$_3$)$_2$CH | (CH$_3$)$_2$CH | phenyl | O | 117–119 |
| 11 | n-C$_3$H$_7$ | n-C$_3$H$_7$ | phenyl | O | 61–63 |
| 12 | phenyl | phenyl | phenyl | O | 240–245 |

TABLE 8-continued

[Structure: HN-C(=O)-Ring B with Z¹-C(Z²)-Y substituent]

| Ref. Ex. No. | Z¹ | Z² | Ring B | Y | M.p. (°C.) |
|---|---|---|---|---|---|
| 13 | n-$C_4H_9$ | n-$C_4H_9$ | (benzene) | $NCH_3$ | 77–78 |
| 14 | $CH_3$ | $CH_3$ | (benzene) | $NCH_3$ | 156–158 |

Effects of the Invention

According to the present invention, the azetidinone compound [III], which is useful as a synthetic intermediate for carbapenem derivatives, is prepared by reacting the alkanamide compound [I] with the compound [II] in the presence of a base without using a Lewis acid.

Especially, when the compound [I] wherein the group of the formula -N($R^2$)($R^3$) is a group of the formula:

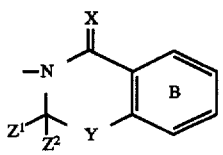

wherein Ring B, X, Y, $Z^1$ and $Z^2$ are the same as defined, and $R^1$ is a lower alkyl group, especially methyl group, is used in the present process, there is stereoselectively obtained the compound of the formula [III-A]:

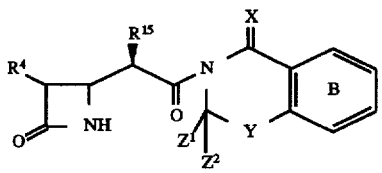

wherein $R^{15}$ is a lower alkyl group and $R^4$, Ring B, X, Y, $Z^1$ and $Z^2$ are the same as defined above, having $R^1$ with β-configuration. Therefore, the present invention can provide a synthetic intermediate useful for 1β-methylcarbapenem derivative having an antibacterial activity.

Besides, the compound [III-A] can be converted into the compound [XII] and the compound [IX] without activating the 4-side chain of the compound [III-A] by chemical modification, and during the reaction from the compound [III-A] to the compound [XII] and the compound [IX], the group of the formula:

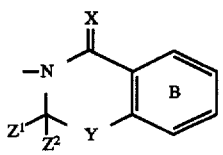

wherein Ring B, X, Y, $Z^1$ and $Z^2$ are the same as defined above, can easily be removed and can be recovered as the compound [IV] after the reaction, and hence, the process for preparing the compound [IX] using the compound [III-A] is extremely excellent process from practical and economical points.

Moreover, the novel alkanamide compound [I-A] can easily be prepared, and in particularly, the compound [I-A] wherein both X and Y are oxygen atom and Ring B is unsubstituted benzene ring is industrially excellent reagent because it can be prepared from a commercially available salicylamide by two steps.

Thus, according to the present process, the azetidinone compound [III], the azetidinonepropionic acid [VI] and the 1β-methylcarbapenem derivative [XI] can be industrially and advantageously prepared at low cost because it is not necessary to perform the optical resolution, to use the expensive Lewis acid, to treat the waste fluid especially, to use the alkylation method, which is difficult to be industrially carried out.

What is claimed is:

1. A compound of the formula (I-A):

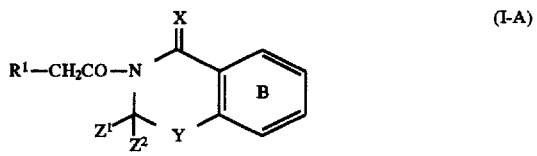
(I-A)

wherein $R^1$ is a lower alkyl group, Ring B is a substituted or unsubstituted benzene ring, X is an oxygen atom or a sulfur atom, Y is an oxygen atom, a sulfur atom, or a protected or unprotected imino group, $Z^1$ and $Z^2$ are the same or different and each a substituted or unsubstituted alkyl group, or an aralkyl group, or both combine at the ends thereof to form a substituted or unsubstituted alkylene group having 4 to 7 carbon atoms.

2. The compound according to claim 1, wherein Y is an oxygen atom or a sulfur atom, $Z^1$ and $Z^2$ are the same or different and each a substituted or unsubstituted alkyl group having 1 to 20 carbon atoms, or both combine at the ends thereof to form a substituted or unsubstituted alkylene group having 4 to 7 carbon atoms.

3. The compound according to claim 1, wherein Ring B is an unsubstituted benzene ring, X is an oxygen atom, Y is an oxygen atom, $Z^1$ and $Z^2$ are the same or different and each a substituted or unsubstituted alkyl group having 1 to 20 carbon atoms, or both combine at the ends thereof to form an unsubstituted alkylene group having 4 to 7 carbon atoms.

* * * * *

UNITED STATES PATENT AND TRADEMARK OFFICE
CERTIFICATE OF CORRECTION

PATENT NO. : 5,703,234
DATED : December 30, 1997
INVENTOR(S) : IWASAKI et al

It is certified that error appears in the above-identified patent and that said Letters Patent is hereby corrected as shown below:

Column 26, lines 64-65 (claim 1, lines 5-6, after the formula), delete "or an aralkyl group,".

Signed and Sealed this

Fifteenth Day of June, 1999

Attest:

Q. TODD DICKINSON

*Attesting Officer*     *Acting Commissioner of Patents and Trademarks*